United States Patent
Yang et al.

(10) Patent No.: US 9,199,964 B1
(45) Date of Patent: Dec. 1, 2015

(54) PROCESS FOR THE PREPARATION OF 3-(3-CHLORO-1H-PYRAZOL-1-YL)PYRIDINE

(71) Applicant: Dow AgroSciences LLC, Indianapolis, IN (US)

(72) Inventors: Qiang Yang, Zionsville, IN (US); Beth Lorsbach, Indianapolis, IN (US); Xiaoyong Li, Midland, MI (US); Gary Roth, Midland, MI (US); David E. Podhorez, Midland, MI (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 14/691,714

(22) Filed: Apr. 21, 2015

Related U.S. Application Data

(63) Continuation of application No. 14/517,315, filed on Oct. 17, 2014.

(60) Provisional application No. 62/031,547, filed on Jul. 31, 2014.

(51) Int. Cl.
| | |
|---|---|
| C07D 231/14 | (2006.01) |
| C07D 403/04 | (2006.01) |
| A01N 43/46 | (2006.01) |
| A61K 31/415 | (2006.01) |
| C07D 401/04 | (2006.01) |

(52) U.S. Cl.
CPC .................................. *C07D 401/04* (2013.01)

(58) Field of Classification Search
CPC .... C07D 231/14; C07D 403/04; A01N 43/46; A61K 31/415
USPC .............. 514/352, 406; 546/275.4; 548/364.1
See application file for complete search history.

(56) References Cited

U.S. PATENT DOCUMENTS

| | | | |
|---|---|---|---|
| 3,597,341 A | 8/1971 | Oswald | |
| 4,080,457 A | 3/1978 | Harrison et al. | |
| 4,260,765 A | 4/1981 | Harrison et al. | |
| 4,407,803 A | 10/1983 | Haviv et al. | |
| 4,536,506 A | 8/1985 | Marcoux et al. | |
| 4,824,953 A | 4/1989 | Bronn | |
| 5,220,028 A | 6/1993 | Iwasawa et al. | |
| 5,625,074 A | 4/1997 | Daum et al. | |
| 5,631,380 A | 5/1997 | Haas et al. | |
| 5,652,372 A | 7/1997 | Muller et al. | |
| 5,693,657 A | 12/1997 | Lee et al. | |
| 5,750,718 A | 5/1998 | Muller et al. | |
| 5,817,677 A | 10/1998 | Linz et al. | |
| 5,854,264 A | 12/1998 | Anthony et al. | |
| 5,854,265 A | 12/1998 | Anthony et al. | |
| 5,869,681 A | 2/1999 | Muller et al. | |
| 6,040,331 A | 3/2000 | Yamamoto et al. | |
| 6,218,418 B1 | 4/2001 | Pevarello et al. | |
| 6,506,747 B1 | 1/2003 | Betageri et al. | |
| 6,548,525 B2 | 4/2003 | Galemmo, Jr. et al. | |
| 6,720,427 B2 | 4/2004 | Sanner et al. | |
| 6,878,196 B2 | 4/2005 | Harada et al. | |
| 6,916,927 B2 | 7/2005 | Bunnage et al. | |
| 6,965,032 B2 | 11/2005 | Freudenberger et al. | |
| 7,192,906 B2 | 3/2007 | Hirohara et al. | |
| 7,196,104 B2 | 3/2007 | Askew, Jr. et al. | |
| 7,319,108 B2 | 1/2008 | Schwink et al. | |
| 7,774,978 B2 | 8/2010 | Ding et al. | |
| 7,803,832 B2 | 9/2010 | Critcher et al. | |
| 7,910,606 B2 | 3/2011 | Nazare et al. | |
| 7,923,573 B2 | 4/2011 | Tamaki et al. | |
| 8,163,756 B2 | 4/2012 | Flynn et al. | |
| 8,222,280 B2 | 7/2012 | Liu et al. | |
| 8,901,153 B2 | 12/2014 | Buysse et al. | |
| 2002/0013326 A1 | 1/2002 | Tiebes et al. | |
| 2003/0153464 A1 | 8/2003 | Nakamura et al. | |
| 2003/0213405 A1 | 11/2003 | Harada et al. | |
| 2004/0043904 A1 | 3/2004 | Yamaguchi et al. | |
| 2004/0082629 A1 | 4/2004 | Iwataki et al. | |
| 2005/0038059 A1 | 2/2005 | Mueller et al. | |
| 2005/0176710 A1 | 8/2005 | Schwink et al. | |
| 2006/0135778 A1 | 6/2006 | Schnatterer et al. | |
| 2006/0160857 A1 | 7/2006 | Buettelmann et al. | |
| 2006/0160875 A1 | 7/2006 | Gaines et al. | |
| 2006/0167020 A1 | 7/2006 | Dickerson et al. | |
| 2006/0287365 A1 | 12/2006 | Billen et al. | |

(Continued)

FOREIGN PATENT DOCUMENTS

| | | |
|---|---|---|
| EP | 0097323 | 1/1984 |
| EP | 0190457 | 8/1986 |

(Continued)

OTHER PUBLICATIONS

Kempe et al., "Responsive Glyco-poly(2-oxaoline)s: Synthesis, Cloud Point Tuning, and Lectin Binding," Biomacromolecules 2011, vol. 12, pp. 2591-2600.
Fields et al., "Preparation of Trifluoromethyl-Pyrazoles and -Pyrazolines by the Reaction of 2,2,2-Trifluorodiazoethane with Carbon—Carbon Multiple Bonds," Journal of Fluorine Chemistry, 1979, vol. 13, pp. 147-158.
Bradbury et al., "Enzyme-catalysed peptide amidation," Eur. J. Biochem. 1987, vol. 169, pp. 579-584.
International Search Report and Written Opinion for PCT/US2014/061005 mailed Dec. 16, 2014.
International Search Report and Written Opinion for PCT/US2014/061006 mailed Dec. 8, 2014.
International Search Report and Written Opinion for PCT/US2014/061007 mailed Dec. 31, 2014.
International Search Report and Written Opinion for PCT/US2014/061009 mailed Dec. 8, 2014.
International Search Report and Written Opinion for PCT/US2014/061010 mailed Dec. 15, 2014.
International Search Report and Written Opinion for PCT/US2014/061012 mailed Dec. 15, 2014.

(Continued)

*Primary Examiner* — Janet L Andres
*Assistant Examiner* — Daniel Carcanague
(74) *Attorney, Agent, or Firm* — Carl D. Corvin; Barnes & Thornburg LLP

(57) ABSTRACT

3-(3-Chloro-1H-pyrazol-1-yl)pyridine is prepared by cyclizing 3-hydrazinopyridine.dihydrochloride with acrylonitrile to provide 1-(pyridin-3-yl)-4,5-dihydro-1H-pyrazol-3-amine, by oxidizing to provide 3-(3-amino-1H-pyrazol-1-yl)pyridine, and by converting the amino group to a chloro group by a Sandmeyer reaction.

12 Claims, No Drawings

(56) References Cited

U.S. PATENT DOCUMENTS

| | | |
|---|---|---|
| 2006/0287541 A1 | 12/2006 | Nishino et al. |
| 2007/0049604 A1 | 3/2007 | Nam et al. |
| 2007/0167426 A1 | 7/2007 | Siddiqui et al. |
| 2008/0004301 A1 | 1/2008 | Tamaki et al. |
| 2008/0027046 A1 | 1/2008 | Annan et al. |
| 2009/0023709 A1 | 1/2009 | Gillespie et al. |
| 2009/0069288 A1 | 3/2009 | Breinlinger et al. |
| 2009/0137524 A1 | 5/2009 | Billen et al. |
| 2009/0325956 A1 | 12/2009 | Taniguchi et al. |
| 2010/0130474 A1 | 5/2010 | Bothmann et al. |
| 2010/0204164 A1 | 8/2010 | Crouse et al. |
| 2010/0286169 A1 | 11/2010 | Guiles et al. |
| 2010/0292253 A1 | 11/2010 | Trullinger et al. |
| 2010/0305200 A1 | 12/2010 | Velicelebi et al. |
| 2011/0021771 A1 | 1/2011 | Mallais et al. |
| 2011/0048261 A1 | 3/2011 | Shimura |
| 2011/0098287 A1 | 4/2011 | Bretschneider et al. |
| 2011/0118290 A1 | 5/2011 | Bretschneider et al. |
| 2011/0166129 A1 | 7/2011 | Machacek et al. |
| 2011/0166143 A1 | 7/2011 | Bretschneider et al. |
| 2011/0184188 A1 | 7/2011 | Wada et al. |
| 2011/0201649 A1 | 8/2011 | Matsuzaki et al. |
| 2011/0212949 A1 | 9/2011 | Bretschneider et al. |
| 2011/0275583 A1 | 11/2011 | Bretschneider et al. |
| 2011/0319428 A1 | 12/2011 | Fublein et al. |
| 2012/0053146 A1 | 3/2012 | Parker et al. |
| 2012/0094837 A1 | 4/2012 | Muhlthau et al. |
| 2012/0095023 A1 | 4/2012 | Bretschneider et al. |
| 2012/0110701 A1 | 5/2012 | Garizi et al. |
| 2012/0110702 A1 | 5/2012 | Yap et al. |
| 2012/0115811 A1 | 5/2012 | Du et al. |
| 2012/0165345 A1 | 6/2012 | Bretschneider et al. |
| 2012/0172218 A1 | 7/2012 | Crouse et al. |
| 2012/0220453 A1 | 8/2012 | Lowe et al. |
| 2012/0252770 A1 | 10/2012 | Berger et al. |
| 2013/0072382 A1 | 3/2013 | Trullinger et al. |
| 2013/0089622 A1 | 4/2013 | Trullinger et al. |
| 2013/0109566 A1 | 5/2013 | Niyaz et al. |
| 2013/0261141 A1 | 10/2013 | Bretschneider et al. |
| 2013/0288893 A1 | 10/2013 | Buysse et al. |
| 2013/0291227 A1 | 10/2013 | Buysse et al. |
| 2013/0324736 A1 | 12/2013 | Ross, Jr. et al. |
| 2013/0324737 A1 | 12/2013 | Ross, Jr. et al. |
| 2013/0338367 A1 | 12/2013 | Numata et al. |
| 2014/0162874 A1 | 6/2014 | Yap et al. |

FOREIGN PATENT DOCUMENTS

| | | |
|---|---|---|
| EP | 0205024 | 12/1986 |
| EP | 0248315 | 12/1987 |
| EP | 0425948 | 5/1991 |
| EP | 1273582 | 1/2003 |
| EP | 1321463 | 6/2003 |
| EP | 1329160 | 7/2003 |
| JP | 1987-153273 | 7/1987 |
| JP | 1988-174905 | 7/1988 |
| JP | 1989-226815 | 9/1989 |
| JP | 2003-212864 | 7/2003 |
| JP | 2004-051628 | 2/2004 |
| JP | 2004-292703 | 10/2004 |
| JP | 2012-188418 | 10/2012 |
| JP | 2013-075871 | 4/2013 |
| JP | 2013-082699 | 5/2013 |
| JP | 2013-082704 | 5/2013 |
| JP | 2013-107867 | 6/2013 |
| JP | 2013-129651 | 7/2013 |
| JP | 2013-129653 | 7/2013 |
| WO | 94/13644 | 6/1994 |
| WO | 97/36897 | 10/1997 |
| WO | 98/49166 | 11/1998 |
| WO | 00/35919 | 6/2000 |
| WO | 01/34127 | 5/2001 |
| WO | 01/90078 | 11/2001 |
| WO | 02/083111 | 10/2002 |
| WO | 03/008405 | 1/2003 |
| WO | 03/072102 | 9/2003 |
| WO | 2004/041813 | 5/2004 |
| WO | 2005/070925 | 8/2005 |
| WO | 2005/074875 | 8/2005 |
| WO | 2006/023462 | 3/2006 |
| WO | 2006/033005 | 3/2006 |
| WO | 2006/046593 | 5/2006 |
| WO | 2006/103045 | 10/2006 |
| WO | 2007/005838 | 1/2007 |
| WO | 2007/087427 | 8/2007 |
| WO | 2007/098826 | 9/2007 |
| WO | 2008/005457 | 1/2008 |
| WO | 2008/079277 | 7/2008 |
| WO | 2008/090382 | 7/2008 |
| WO | 2009/149858 | 12/2009 |
| WO | 2010/006713 | 1/2010 |
| WO | 2010/009290 | 1/2010 |
| WO | 2010/012442 | 2/2010 |
| WO | 2010/033360 | 3/2010 |
| WO | 2010/048207 | 4/2010 |
| WO | 2010/060379 | 6/2010 |
| WO | 2010/075376 | 7/2010 |
| WO | 2010/129497 | 11/2010 |
| WO | 2010/133336 | 11/2010 |
| WO | 2010/146236 | 12/2010 |
| WO | 2011/003065 | 1/2011 |
| WO | 2011/043371 | 4/2011 |
| WO | 2011/045224 | 4/2011 |
| WO | 2011/045240 | 4/2011 |
| WO | 2011/091153 | 7/2011 |
| WO | 2011/101229 | 8/2011 |
| WO | 2011/126903 | 10/2011 |
| WO | 2011/128304 | 10/2011 |
| WO | 2011/134964 | 11/2011 |
| WO | 2011/138285 | 11/2011 |
| WO | 2011/163518 | 12/2011 |
| WO | 2012/000896 | 1/2012 |
| WO | 2012/004217 | 1/2012 |
| WO | 2012/007500 | 1/2012 |
| WO | 2012/035011 | 3/2012 |
| WO | 2012/052412 | 4/2012 |
| WO | 2012/061290 | 5/2012 |
| WO | 2012/070114 | 5/2012 |
| WO | 2012/102387 | 8/2012 |
| WO | 2012/108511 | 8/2012 |
| WO | 2012/147107 | 11/2012 |
| WO | 2012/168361 | 12/2012 |
| WO | 2013/000931 | 1/2013 |
| WO | 2013/010946 | 1/2013 |
| WO | 2013/010947 | 1/2013 |
| WO | 2013/062980 | 5/2013 |
| WO | 2013/064324 | 5/2013 |
| WO | 2013/156431 | 10/2013 |
| WO | 2013/156433 | 10/2013 |

OTHER PUBLICATIONS

International Search Report and Written Opinion for PCT/US2014/061014 mailed Dec. 15, 2014.

International Search Report and Written Opinion for PCT/US2014/061016 mailed Dec. 15, 2014.

International Search Report and Written Opinion for PCT/US2014/061022 mailed Dec. 29, 2014.

International Search Report and Written Opinion for PCT/US2014/061023 mailed Dec. 15, 2014.

International Search Report and Written Opinion for PCT/US2014/061024 mailed Dec. 15, 2014.

International Search Report and Written Opinion for PCT/US2014/061027 mailed Dec. 15, 2014.

International Search Report and Written Opinion for PCT/US2014/061029 mailed Dec. 15, 2014.

International Search Report and Written Opinion for PCT/US2014/061030 mailed Dec. 15, 2014.

International Search Report and Written Opinion for PCT/US2013/029615 mailed May 8, 2013.

PROCESS FOR THE PREPARATION OF 3-(3-CHLORO-1H-PYRAZOL-1-YL)PYRIDINE

CROSS REFERENCE TO RELATED APPLICATIONS

This application is a continuation of U.S. application Ser. No. 14/517,315 filed on Oct. 17, 2014, which claims the benefit of U.S. Provisional Patent Application Ser. No. 62/031,547, filed Jul. 31, 2014, the entire disclosures of which are hereby expressly incorporated by reference in this Application.

BACKGROUND

The present invention concerns an improved process for preparing 3-(3-chloro-1H-pyrazol-1-yl)pyridine.

US 20130288893(A1) describes, inter alia, certain (3-halo-1-(pyridin-3-yl)-1H-pyrazol-4-yl)amides and carbamates and their use as pesticides. The route to prepare such compounds involved the preparation of 3-(3-chloro-1H-pyrazol-1-yl)pyridine (5b) by the direct coupling of 3-bromopyridine with 3-chloropyrazole. The 3-chloropyrazole was prepared by a) treating 1H-pyrazole with 2-dimethylsulfamoyl chloride and sodium hydride to provide N,N-dimethyl-1H-pyrazole-1-sulfonamide, b) treating the N,N-dimethyl-1H-pyrazole-1-sulfonamide with perchloroethane and n-butyl lithium to provide 3-chloro-N,N-dimethyl-1H-pyrazole-1-sulfonamide, and c) removing the N,N-dimethylsulfonamide from 3-chloro-N,N-dimethyl-1H-pyrazole-1-sulfonamide with trifluoroacetic acid to give the 3-chloropyrazole.

The disclosed process produces low yields, relies on a starting material that is difficult to prepare (3-chloropyrazole) and provides a product that is difficult to isolate in a pure form. It would be desirable to have a process for preparing 3-(3-chloro-1H-pyrazol-1-yl)pyridine that avoids these problems.

SUMMARY

The present invention provides such an alternative by cyclizing 3-hydrazinopyridine.dihydrochloride with acrylonitrile to provide 1-(pyridin-3-yl)-4,5-dihydro-1H-pyrazol-3-amine (9a), by oxidizing to provide 3-(3-amino-1H-pyrazol-1-yl)pyridine (8a), and by converting the amino group to a chloro group by a Sandmeyer reaction. Thus, the present invention concerns a process for preparing 3-(3-chloro-1H-pyrazol-1-yl)pyridine (5b),

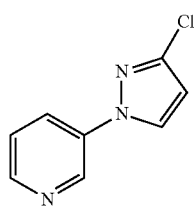

(5b)

which comprises a) treating 3-hydrazinopyridine.dihydrochloride

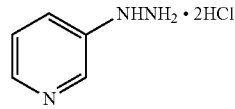

with acrylonitrile

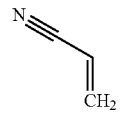

in a ($C_1$-$C_4$) aliphatic alcohol at a temperature of about 25° C. to about 100° C. in the presence of an alkali metal ($C_1$-$C_4$) alkoxide to provide 1-(pyridin-3-yl)-4,5-dihydro-1H-pyrazol-3-amine (9a)

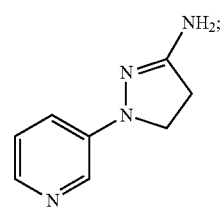

(9a)

b) treating the 1-(pyridin-3-yl)-4,5-dihydro-1H-pyrazol-3-amine (9a) with an oxidant in an inert organic solvent at a temperature of about 25° C. to about 100° C. to provide 3-(3-amino-1H-pyrazol-1-yl)pyridine (8a)

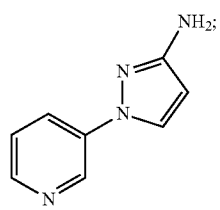

(8a)

c) treating the 3-(3-amino-1H-pyrazol-1-yl)pyridine (8a) in aqueous hydrochloric acid with sodium nitrite at a temperature of about 0° C. to about 25° C. to provide the diazonium salt (8b)

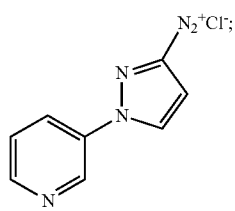

(8b)

and d) treating the diazonium salt (8b) with copper chloride at a temperature of about 0° C. to about 25° C.

DETAILED DESCRIPTION

The present invention provides an improved process for preparing 3-(3-chloro-1H-pyrazol-1-yl)pyridine (5b), by cyclizing 3-hydrazinopyridine.dihydrochloride with acrylonitrile to provide 1-(pyridin-3-yl)-4,5-dihydro-1H-pyrazol-3-amine (9a), by oxidizing to provide 3-(3-amino-1H-pyrazol-1-yl)pyridine (8a), and by converting the amino group to a chloro group by a Sandmeyer reaction.

In the first step, 3-hydrazinopyridine.dihydrochloride is treated with acrylonitrile in a ($C_1$-$C_4$) aliphatic alcohol at a temperature of about 25° C. to about 100° C. in the presence of an alkali metal ($C_1$-$C_4$) alkoxide to provide 1-(pyridin-3-yl)-4,5-dihydro-1H-pyrazol-3-amine. While stoichiometric amounts of 3-hydrazinopyridine.dihydrochloride and acrylonitrile are required, it is often convenient to use about a 1.5 fold to about a 2 fold excess of acrylonitrile. The cyclization is run in the presence of an alkali metal ($C_1$-$C_4$) alkoxide base. It is often convenient to use about a 2 fold to about a 5 fold excess of base. The cyclization is performed in a ($C_1$-$C_4$) aliphatic alcohol. It is most convenient that the alkoxide base and the alcohol solvent be the same, for example, sodium ethoxide in ethanol.

In a typical reaction, 3-hydrazinopyridine.dihydrochloride and an anhydrous alcohol are introduced into a reaction vessel and the alkoxide base is gradually added. The mixture is stirred and the acrylonitrile is added. The mixture is stirred at about 60° C. until most of the 3-hydrazinopyridine has reacted. The mixture is allowed to cool and the excess base is neutralized with acid. The crude 1-(pyridin-3-yl)-4,5-dihydro-1H-pyrazol-3-amine (9a) is conveniently isolated and purified by standard techniques.

In the second step, 1-(pyridin-3-yl)-4,5-dihydro-1H-pyrazol-3-amine (9a) is treated with an oxidant in an organic solvent at a temperature of about 25° C. to about 100° C. to provide 3-(3-amino-1H-pyrazol-1-yl)pyridine (8a). Suitable oxidants include manganese(IV) oxide, potassium ferricyanide(III), copper(I) chloride in the presence of oxygen, and iron(III) chloride in the presence of oxygen. Manganese(IV) oxide is preferred. It is often convenient to use about a 2 fold to about a 10 fold excess of oxidant. The oxidation is performed in a solvent that is inert to the oxidant. Suitable solvents include nitriles such as acetonitrile or halocarbons such as dichloromethane. With manganese(IV) oxide as the oxidant, acetonitrile is a preferred solvent.

In a typical reaction, 1-(pyridin-3-yl)-4,5-dihydro-1H-pyrazol-3-amine (9a) and solvent are mixed with the oxidant and the mixture is heated at about 60° C. until the reaction is completed. The 3-(3-amino-1H-pyrazol-1-yl)pyridine (8a) is conveniently isolated and purified by standard techniques.

The 3-(3-amino-1H-pyrazol-1-yl)pyridine (8a) is then converted to the desired 3-(3-chloro-1H-pyrazol-1-yl)pyridine (5b) by treatment in aqueous hydrochloric acid with sodium nitrite at a temperature of about 0° C. to about 25° C. to provide a diazonium salt followed by treatment of the diazonium salt with copper chloride at a temperature of about 0° C. to about 25° C. While stoichiometric amounts of reagents are required, it is often convenient to use an excesses of reagents with respect to the 3-(3-amino-1H-pyrazol-1-yl)pyridine (8a). Thus, aqueous hydrochloric acid is used in large excess as the reaction medium. Sodium nitrite is used in about a 1.3 fold to about a 2 fold excess. Copper chloride is used in about 5 mole percent to about 60 mole percent excess, preferably from about 15 mole percent to about 30 mole percent excess. The copper chloride may be either copper(I) chloride or copper(II) chloride. To suppress foaming during the reaction a water-immiscible organic solvent such as toluene or chloroform can be added during the treatment of the diazonium salt with copper chloride.

In a typical reaction, a mixture of 3-(3-amino-1H-pyrazol-1-yl)pyridine (8a) and aqueous hydrochloric acid are mixed and cooled to about 0° C. An aqueous solution of sodium nitrite is slowly added maintaining the temperature below about 5° C. The suspension is stirred at about 0° C. for about 2 hours. In a separate vessel, a mixture of copper(II) chloride and toluene is cooled to about 0° C. and the chilled suspension of diazonium salt is added at a rate maintaining the temperature below about 5° C. The mixture is allowed to warm to about ambient temperature. After completion of the reaction, the mixture is treated with aqueous sodium hydroxide to adjust the pH to about 8 to about 10. The resulting solution is extracted with a water-immiscible organic solvent. After removal of the solvent, the 3-(3-chloro-1H-pyrazol-1-yl)pyridine (5b) can be used directly in the next reaction or further purified by standard techniques such as flash column chromatography or crystallization.

The following examples are presented to illustrate the invention.

Examples

1. Preparation of 1-(pyridin-3-yl)-4,5-dihydro-1H-pyrazol-3-amine (9a)

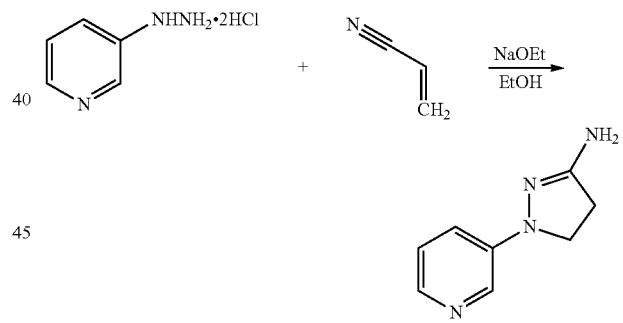

To a 4-neck, round bottomed flask (250 mL) was charged sodium ethanolate (21 wt % in ethanol, 32 mL). 3-Hydrazinopyridine-dihydrochloride (5.00 g, 27.5 mmol) was added, causing an exotherm from 20° C. to 58° C. The mixture was allowed to cool to 20° C. and acrylonitrile (2.91 g, 54.9 mmol) was added. The reaction was heated at 60° C. for 5 hours and cooled to 20° C. The excess sodium ethanolate was quenched with hydrochloric acid (4 M in 1,4-dioxane, 6.88 mL, 27.5 mmol) at <20° C. The mixture was adsorbed on silica gel (10 g) and the crude product was purified by flash column chromatography using 0-10% methanol/dichloromethane as eluent. The fractions containing pure product were concentrated to dryness to afford the title compound as a yellow solid (3.28 g, 74%): mp 156-160° C.; $^1$H NMR (400 MHz, CDCl$_3$) δ 8.24 (dd, J=2.8, 0.8 Hz, 1H), 8.01 (dd, J=4.6, 1.4 Hz, 1H), 7.22 (ddd, J=8.4, 2.8, 1.5 Hz, 1H), 7.12 (ddd, J=8.4, 4.6, 0.8 Hz, 1H), 4.20 (s, 2H), 3.70 (t, J=9.3 Hz, 2H), 2.92 (t, J=9.3 Hz, 2H); $^{13}$C NMR (101 MHz, CDCl$_3$) δ 154.23, 144.78, 139.22, 135.08, 123.44, 119.44, 49.23, 32.74; ESIMS m/z 163 ([M+H]$^+$).

2. Preparation of 3-(3-amino-1H-pyrazol-1-yl)pyridine (8a)

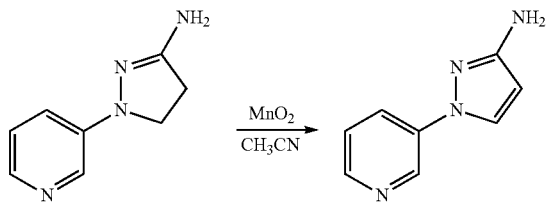

To a 3-neck, round bottomed flask (100 mL) was charged 1-(pyridin-3-yl)-4,5-dihydro-1H-pyrazol-3-amine (1.00 g, 6.17 mmol) and acetonitrile (20 mL). Manganese(IV) oxide (2.68 g, 30.8 mmol) was added, causing an exotherm from 20° C. to 25° C. The reaction was stirred at 60° C. for 18 hours, after which it was filtered through a Celite® pad and the pad was rinsed with acetonitrile (20 mL). Water (20 mL) was added to the combined filtrates and the resulting mixture was concentrated to 10 mL. Water (20 mL) was added and the resulting mixture was again concentrated to 10 mL. The resulting suspension was stirred at 20° C. for 18 hours and filtered. The filter cake was rinsed with water (2×5 mL) and dried to afford the title compound as a brown solid (0.68 g, 69%): mp 169-172° C.; $^1$H NMR (400 MHz, DMSO-d$_6$) δ 9.07-8.82 (m, 1H), 8.33 (dd, J=4.6, 1.5 Hz, 1H), 8.24 (d, J=2.6 Hz, 1H), 8.00 (ddd, J=8.4, 2.7, 1.4 Hz, 1H), 7.42 (ddd, J=8.5, 4.6, 0.8 Hz, 1H), 5.80 (d, J=2.6 Hz, 1H), 5.21 (s, 2H); $^{13}$C NMR (101 MHz, DMSO-d$_6$) δ 157.67, 144.68, 138.00, 136.22, 128.30, 123.95, 123.17, 97.08; ESIMS m/z 161 ([M+H]$^+$).

3. Preparation of 3-(3-chloro-1H-pyrazol-1-yl)pyridine (5b)

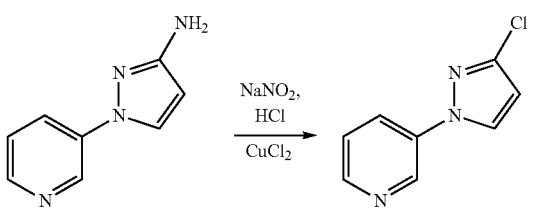

To a 3-neck round bottomed flask (250 mL) was charged 3-(3-amino-1H-pyrazol-1-yl)pyridine (5.00 g, 31.2 mmol) and hydrogen chloride (37 wt %, 15 mL). The mixture was cooled to 0° C. A solution of sodium nitrite (4.31 g, 62.4 mmol) in water (15 mL) was added in portions at <1° C. over 20 minutes and the resulting brown solution was stirred at <0° C. for 2 hours. To a separate 3-neck round bottomed flask (250 mL) was charged copper(II) chloride (5.04 g, 37.5 mmol) and toluene (30 mL). It was cooled to 0° C. and the yellow solution was added in portions at <1° C. over 15 minutes. The resulting mixture was allowed to warm up, off-gassing was observed when the reaction temperature reached 18° C. The reaction was stirred at 20° C. for 18 hours. The reaction was basified with 50 wt % sodium hydroxide to pH ~10. Celite® (10 g) was added and the resulting suspension was stirred for 10 minutes. The suspension was filtered through a Celite® pad (10 g) and the filter cake was rinsed with ethyl acetate (2×50 mL). The layers of the filtrates were separated and the aqueous layer was extracted with ethyl acetate (100 mL). The organic layers were concentrated to dryness and the residue was purified by flash column chromatography using 0-60% ethyl acetate/hexanes as eluent. The fractions containing the desired product were concentrated to give the title compound as a white solid (3.80 g, 68%): mp 104-106° C.; $^1$H NMR (400 MHz, CDCl$_3$) δ 8.93 (d, J=2.7 Hz, 1H), 8.57 (dd, J=4.8, 1.4 Hz, 1H), 8.02 (ddd, J=8.3, 2.7, 1.5 Hz, 1H), 7.91 (d, J=2.6 Hz, 1H), 7.47-7.34 (M, 1H), 6.45 (d, J=2.6 Hz, 1H); $^{13}$C NMR (101 MHz, CDCl$_3$) δ 148.01, 142.72, 140.12, 135.99, 128.64, 126.41, 124.01, 108.08; EIMS m/z 179 ([M]$^+$).

What is claimed is:
1. A process for preparing 3-(3-chloro-1H-pyrazol-1-yl)pyridine (5b),

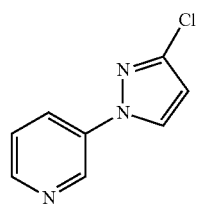

which comprises
a) treating 3-hydrazinopyridine.dihydrochloride

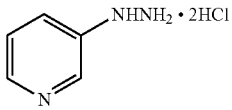

with about 1 to about 2 equivalents of acrylonitrile

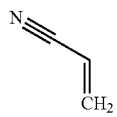

in a (C$_1$-C$_4$) aliphatic alcohol at a temperature of about 25° C. to about 100° C. in the presence of about a 2-fold to about a 5-fold excess of an alkali metal (C$_1$-C$_4$) alkoxide to provide 1-(pyridin-3-yl)-4,5-dihydro-1H-pyrazol-3-amine (9a)

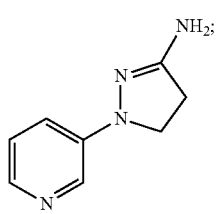

b) treating the 1-(pyridin-3-yl)-4,5-dihydro-1H-pyrazol-3-amine (9a) with about a 2-fold to about a 10-fold excess of an oxidant in an organic solvent at a temperature of about 25° C. to about 100° C. to provide 3-(3-amino-1H-pyrazol-1-yl)pyridine (8a)

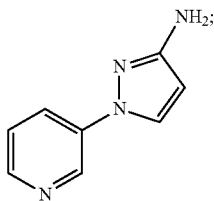
(8a)

c) treating the 3-(3-amino-1H-pyrazol-1-yl)pyridine (8a) with an excess of aqueous hydrochloric acid and about a 1.3-fold to about a 2-fold excess of sodium nitrite at a temperature of about 0° C. to about 25° C. to provide the diazonium salt (8b)

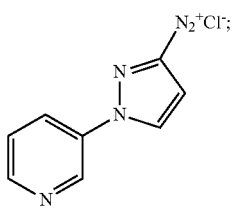
(8b)

and d) treating the diazonium salt (8b) with about 5 mole percent to about 60 mole percent of copper chloride at a temperature of about 0° C. to about 25° C.

2. The process of claim 1 in which the oxidant is manganese(IV) oxide, potassium ferricyanide (III), copper(I) chloride in the presence of oxygen, or iron(III) chloride in the presence of oxygen.

3. The process of claim 2 in which the oxidant is manganese(IV) oxide.

4. The process of claim 3, wherein the organic solvent of step (b) is acetonitrile.

5. The process of claim 1, wherein the copper chloride is in an amount of about 15 mole percent to about 30 mole percent.

6. The process of claim 5, wherein the copper chloride is copper (I) chloride or copper (II) chloride.

7. The process of claim 5, wherein the copper chloride is copper (I) chloride.

8. The process of claim 5, wherein the copper chloride is copper (II) chloride.

9. The process of any one of claims 6 to 8, wherein a water immiscible organic solvent is added in step d) to suppress foaming.

10. The process of claim 9, wherein the water immiscible solvent is toluene.

11. The process of claim 1, wherein the step (a) ($C_1$-$C_4$) aliphatic alcohol and the ($C_1$-$C_4$) alkoxide have the same $C_1$-$C_4$ group.

12. The process of claim 11, wherein the step (a) ($C_1$-$C_4$) aliphatic alcohol is ethanol and the ($C_1$-$C_4$) alkoxide is sodium ethoxide.

* * * * *